United States Patent [19]

Benetti et al.

[11] Patent Number: 4,786,470

[45] Date of Patent: Nov. 22, 1988

[54] ALUMINUM-BRONZE DENTAL ALLOY

[75] Inventors: Giulio Benetti, Suisun, Vincent M. Benetti, Benecia, both of Calif.

[73] Assignee: Aalba Dent, Inc., Concord, Calif.

[21] Appl. No.: 63,836

[22] Filed: Jun. 19, 1987

[51] Int. Cl.⁴ ............................................. C22C 9/01
[52] U.S. Cl. ................................... 420/479; 420/480; 433/207
[58] Field of Search ...................... 420/478, 479, 480

[56] References Cited

U.S. PATENT DOCUMENTS

| 38,301 | 4/1862 | Farmer | 420/478 |
|---|---|---|---|
| 1,764,034 | 6/1930 | Palm | 420/478 |
| 3,252,793 | 5/1966 | Hesse | 420/479 |
| 3,753,696 | 8/1973 | Shibata et al. | 420/478 |

Primary Examiner—L. Dewayne Rutledge
Assistant Examiner—George Wyszomierski
Attorney, Agent, or Firm—Limbach, Limbach & Sutton

[57] ABSTRACT

A new aluminum-bronze dental alloy and restoration technique is disclosed in which castability and burnishability are improved by the presence of 1 to 8 percent zinc.

2 Claims, 1 Drawing Sheet

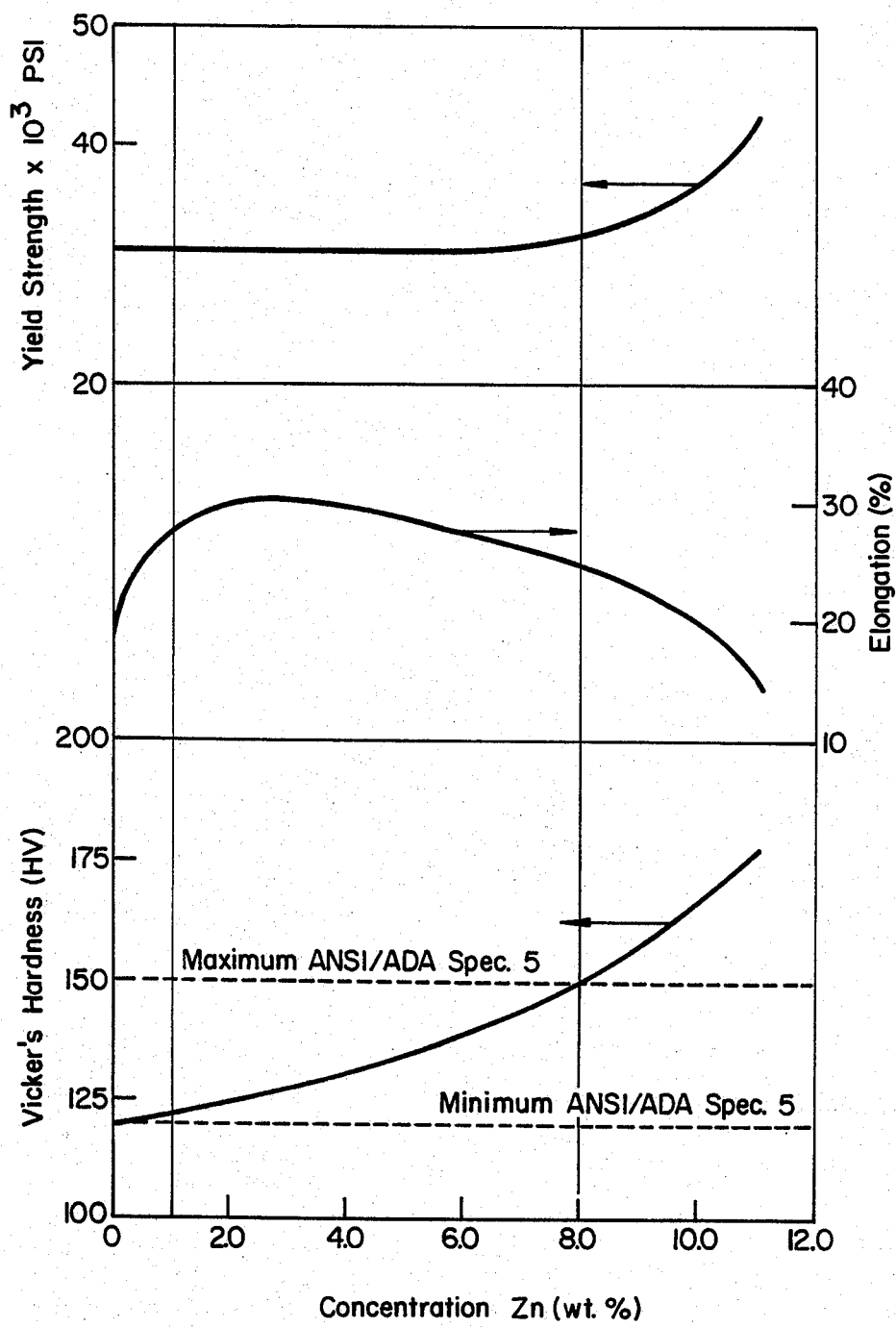
FIG._1.

ALUMINUM-BRONZE DENTAL ALLOY

BACKGROUND OF THE INVENTION

This invention relates to non-precious metal alloys useful for the manufacture of dental restorations. In particular it relates to the improvement of copper-aluminum alloys with small amounts of zinc.

There can be no doubt that high gold content alloys are the ideal metal for the casting of dental restorations because they have a combination of properties unequaled by any other element. However, as the price of gold has increased in recent years, efforts have been made to reduce the amount of gold used so that dental restorations are affordable to the average person. Reducing the percentage of gold in an alloy is not a satisfactory solution because the desired properties are lost if the amount of gold is reduced to a percentage where the casting might be affordable. Gold is at least ten times as expensive as any nonprecious elements, so there has been great interest in developing alloys made entirely of non-precious metals.

At least as early as 1922 (Hepburn "Notes on Dental Metallurgy"), workers in the dental restoration field have explored aluminum-bronze alloys as a substitution for gold. However, oxidation and galvanic properties encountered in the oral environment usually led to the rejection of these substitutions (Thomson, et al. 50, J. Prosthetic Dentistry, 654 (November 1983)). Specifically the marginal fit of cast copings has not been acceptable in prior art high-copper castings.

While the chemical and physical properties of gold presently to be described are essential to its performance in the mouth under demanding conditions, there is one property that is insisted upon by many consumers: the gold color. Many attempts to emulate the color of gold in a dental alloy have been made. Perhaps the most successful have been copper alloys because the gold color can be achieved with appropriate blending of other metals with copper. Unfortunately, copper alloys have two shortcomings as now formulated. First, the castability is not as good as high gold alloys. Gold alloys are eminently castable, but copper alloys now on the market are not satisfactory. Various elements have been combined with copper in an attempt to improve castability, but the combinations have not been entirely successful.

The second shortcoming of copper alloys for dental restorations has been corrosion. As has been known for centuries, the desired copper color gives way to a green color upon oxidation or corrosion. More importantly, in vivo corrosion results in progressive dissolution of the casting in the oral evironment.

The regulation of dental alloys is highly developed. The standard of comparisons for mechanical properties is ANSI/ADA Spec. No. 5 for Dental Casting Gold Alloy, Type III (hard). Another clinically relevant mechanical property is burnishability (Moon et al., "The Burnishability of Dental Casting Alloys", J. Prosthet. Dent. 36:404-8 (October 1976)).

Corrosion resistance may be compared to existing dental alloys on the market, such as high copper content alloy called "Sybraloy" (Kerr-Sybron), an amalgam alloy certified by the American Dental Association, which has relatively poor corrosion resistance (though clinically acceptable) compared to precious metal alloys. There is on the market lowered gold content Type III casting alloys, such as one called "Minigold" (Williams-Ivoclar), which have relatively poor corrosion resistance for a gold alloy. There is a need for a copper-containing alloy with corrosion resistance superior to known copper-containing alloys like Sybraloy and approaching the corrosion resistance of a precious metal alloy like Minigold.

In addition, it is essential for any dental alloy to be castable for making dental restorations, and non-toxic in the mouth. The latter quality is often measured by the Agar Diffusion Cytotoxicity test to assure an acceptable biological response.

There is a need for a dental alloy having the chemical and physical properties of gold, and with the color of gold, but at a price below the prohibitive cost of gold.

The properties thus sought are:
1. Mechanical properties
2. Biological response
3. Castability
4. Corrosion resistance
5. Gold color
6. Low cost.

SUMMARY OF THE PRESENT INVENTION

The present invention relates to a non-precious metal alloy suitable as a replacement for gold in dental restorations. The alloy contains copper, aluminum, iron, nickel, zinc and manganese. The primary difference from existing copper-based alloys is the presence of zinc in the alloy of the present invention, whereas other alloys do not have this element present. The zinc improves the castability, burnishability, and biocompatibility of the alloy, and, at lower zinc levels, improves corrosion resistance as well.

The alloy of the present invention is a yellow-gold colored, non-precious "Type III" casting alloy for use in the construction of crowns, bridges, inlays and onlays. Fabrication of a cast restoration with this alloy requires no new or special techniques. It finishes easily and takes a high, lustrous polish.

It is exceedingly difficult to quantify the effect of variations of every element in an alloy containing zinc, copper, aluminum, iron, nickel and manganese as far as biocompatibility, physical properties and the like are concerned. Consequently, the present invention is presented as an addition of variable amounts of zinc to an alloy of Cu, Al, Fe, Ni and Mn as constants. This does not mean that variations in the other elements is not within the contemplation of the invention even though the non-variable elements are presented as constants. In other words, equivalent alloys are intended to be within the scope of the invention, even though the presentation is in terms of variations of zinc content.

With this caveat, the present invention contemplates a dental alloy with 7.0 to 9.0% aluminum; 0–5.5% iron; 3.0–5.5% nickel; 0–2.5% manganese; and the balance of the constant as copper. The variable is the amount of zinc added to the alloy, being at least 1% and not more than 8% of the weight of the alloy. As is well known in the art, the manufacture of a six-component alloy with one variable and five constant components is a virtual impossibility. Accordingly, the non-zinc components in the examples are intended to be constant, but practical expediency suggests slight variations in the "constant" elements present.

In the preferred embodiments, aluminum should be present in an amount between 7.0% and 9.0% of the weight of the composition. Nickel should be present in an amount between 3.0 and 5.5%. Zinc should be present in an amount between 1.5 and 3.5%. Iron and manganese are not essential to the effectiveness of the alloy, but it is preferred to add iron in an amount up to 5.0% and manganese in an amount up to 2.5% of the weight of the composition. Copper makes up the balance of the alloy.

DESCRIPTION OF THE PREFERRED EMBODIMENTS

All of the formulations of the present alloy comply with the mechanical property requirements of ANSI/ADA Specification No. 5 for dental casting gold alloy, Type III (hard). The elongation of the alloy is an important property, and elongation increases with increasing zinc concentration. Hardness is another important property. According to the ANSI/ADA Spec. 5, hardness must be between 120 and 150 on the Vickers scale. The present alloy has a Vickers hardness of 140.

Hardness and elongation can be combined to measure burnishability. Generally speaking, non-precious alloys have a poorer initial fit than gold-based alloys, and it is important that the gold substitutes be burnishable. The burnishability index number is derived from the hardness divided by the percent of elongation. The additions of zinc to the alloy greatly enhances its burnishability.

All formulations of the present alloy were found to be non-cytotoxic using the Agar Diffusion Cytotoxicity cell culture test. Rabbit muscle implant tests showed a response similar to conventional dental restorations materials used in the oral environment.

Castability of the present alloy is superior to other known copper-based alloys. Corrosion resistance is also superior where zinc content of the formulations is 5% or less.

Table 1 shows a comparison between the alloy of this invention and two of the more popular copper-based alloys in the dental market today. One is called MS, made in Brazil and marketed in the U.S. by Monarch Metals Corp. and distributed by Preat Corporation, 191 West 25th Ave. San Mateo, Calif. 94403. The other is called Trindium made by Trindium Corporation of America, P.O. Box 95, Sauquoit, N.Y, 13456.

TABLE 1

| Element | New Alloy % | MS % | Trindium % |
|---|---|---|---|
| Al | 7.0–9.0 | 7.82 | 9.02 |
| Cu | Balance | 81.90 | 89.60 |
| Fe | 0.0–5.0 | 4.04 | Trace |
| Mn | 0.0–2.5 | 1.56 | Trace |
| Ni | 3.0–5.5 | 4.31 | 1.30 |
| Si | — | 0.12 | Trace |
| Zn | 1.0–8.0 | Trace | Trace |

Three specific examples of alloys made in accordance with the present invention are shown in Table 2. The elements other than zinc are essentially constant, with percentages declining as the zinc content increases from Example 1 to Example 3.

TABLE 2

| | Cu | Al | Fe | Mn | Ni | Zn |
|---|---|---|---|---|---|---|
| Example 1 | 80.2 | 7.70 | 4.11 | 1.42 | 4.68 | 1.80 |
| Example 2 | 79.3 | 7.89 | 3.94 | 1.47 | 4.39 | 3.04 |
| Example 3 | 77.5 | 7.41 | 3.66 | 1.54 | 4.16 | 5.75 |

The mechanical properties of yield strength, elongation and hardness of the alloy have been plotted in FIG. 1. It will be seen that hardness increases as zinc content increases. While hardness meets the Spec. 5 minimum even if the alloy has no zinc, a zinc content of about 1% improves other properties of the alloy. Beyond about 8% zinc content, the hardness exceeds the maximum of Spec. 5, placing the upper limit of zinc in the alloy at that level.

Likewise, elongation is well above 20% with the alloy formulated with 1–8% zinc, whereas comparable copper-based alloys on the market have an elongation value of around 12%. Elongation and hardness qualities make this alloy optimally burnishable. The burnishability index for the alloy of Example 1 (Table 2) is 3.23. For Example 2, it is 3.59. For Example 3, it is 3.93. All 3 examples compare favorably with gold alloys.

Yield strength of the alloy remains fairly constant as shown in FIG. 1 until the zinc content exceeds the upper limit of 8% in the formulation. By maintaining zinc at a level between one and eight percent, both mechanical and other properties are optimized.

Related to the foregoing mechanical properties is the castability of the alloy. We have found all formulations of this alloy to be highly castable using the procedures described in Mitchell and Kemper "Castability of Ni-Cr Alloys Using a Fine-Gauge Mesh Test (Dept. of Restorative Dentistry, University of Kentucky, March 1984). A standard 15 mm×15 mm mesh casting pattern of ASTM No. 50 sieve cloth was used. Patterns were cast at a constant mold temperature and a constant induction casting machine setting. The percent of fill of the pattern was measured for each of Examples 1, 2 and 3, and comparison was made with MS and Trindium, as before. The alloy of Example 1 had a mean value of 80.0%; Example 2 had 93.2%; and Example 3 had 71.5% fill. MS and Trindium were both under 80, as was a 46% gold alloy also examined for comparison. It is preferred to have zinc present in an amount between 2.5% and 4.5% for castability, although zinc content up to 8.0% is satisfactory.

It has also been found that corrosion resistance is improved with zinc values at 5% or less, presumably because a passive layer is formed on the casting. However, the presence of zinc at values over about 7% appears to result in generalized progressive corrosion.

Thus, the preferred composition has between 1.8 and 5.75% zinc to gain the greatest advantages available from the alloy. As close as we can determine, the best zinc content in the alloy is between 2.5–3.0%.

Because of the known selective dissolution of copper from low gold casting alloys (e.g. 40% gold, 7.5% copper), biological tests were conducted on the present alloy. In an Agar Diffusion Cytotoxicity test, the present alloy was found not to be cytotoxic, unlike other copper-containing alloys. The presence of zinc apparently makes the alloy safer for its intended use than if it is not present.

Another biological test conducted on the present alloy was a rabbit muscle implant study. The back muscle of a rabbit was implanted with the alloy, the metal was retrieved, and the response studied. There was no gross pathology, but each sample showed slight histopathology. There was no necrosis evident, but there was slight toxicity, not incompatible with use as a casting alloy in the oral environment. It was concluded that this alloy is compatible with health when used as a dental restorative.

In clinical tests on 20 patients, no evidence of tarnish or corrosion or any change in the condition of soft tissue contacted with the restoration of this invention was found. Patients did not experience any thermal sensitivity or unusual taste.

While the benefits of the present invention are shown in the alloys of the ranges shown, it will be appreciated by those skilled in the art that equivalent variations may also be used.

We claim:

1. A dental alloy consisting essentially of 7.0 to 9.0% aluminum, 3.0 to 5.5% nickel, up to 5.0% iron, up to 2.5% manganese, 1.8 to 5.75% zinc, and the balance copper.

2. A dental alloy as in claim 1 wherein zinc is present in an amount between 2.5 and 3.0%.

* * * * *